(12) United States Patent
Kelley

(10) Patent No.: US 6,593,572 B2
(45) Date of Patent: Jul. 15, 2003

(54) METHOD OF PREDICTING MECHANICAL PROPERTIES OF DECAYED WOOD

(75) Inventor: Stephen S. Kelley, Evergreen, CO (US)

(73) Assignee: Midwest Research Institute, Kansas City, MO (US)

( * ) Notice: Subject to any disclaimer, the term of this patent is extended or adjusted under 35 U.S.C. 154(b) by 0 days.

(21) Appl. No.: 09/900,313

(22) Filed: Jul. 6, 2001

(65) Prior Publication Data

US 2002/0109093 A1 Aug. 15, 2002

Related U.S. Application Data

(63) Continuation-in-part of application No. 09/740,293, filed on Dec. 15, 2000, and a continuation-in-part of application No. 09/738,912, filed on Dec. 13, 2000.

(51) Int. Cl.$^7$ ............................................. G01T 5/02
(52) U.S. Cl. ............................. 250/339.05; 250/339.07
(58) Field of Search ....................... 250/339.05, 339.07, 250/339.09, 343; 356/73, 343; 700/129; 702/30

(56) References Cited

U.S. PATENT DOCUMENTS

| | | | |
|---|---|---|---|
| 4,606,645 A | * 8/1986 | Matthews et al. | 356/446 |
| 4,802,762 A | * 2/1989 | Hill, Jr. | 356/318 |
| 4,885,709 A | * 12/1989 | Edgar et al. | 364/563 |
| 5,536,942 A | 7/1996 | Barringer et al. | 250/339.12 |
| 5,638,284 A | 6/1997 | Helmer et al. | 364/498 |
| 5,680,320 A | 10/1997 | Helmer et al. | 364/498 |
| 5,680,321 A | 10/1997 | Helmer et al. | 364/499 |
| 5,945,676 A | 8/1999 | Khalil et al. | 250/339.12 |
| 5,965,888 A | 10/1999 | Engstrom et al. | 250/339.09 |
| 6,031,233 A | 2/2000 | Levin et al. | 250/339.11 |
| 6,122,042 A | * 9/2000 | Wunderman et al. | 356/73 |

OTHER PUBLICATIONS

Brown, S.D., "Chemometrics", Anal. Chem. 62, 84R–101R (1990).

Hoffmeyer, P., et al., Holz als Roh–und Werkstoff 53 (1995) 165–170 (Density and Strength from a Dry Sample).

* cited by examiner

Primary Examiner—Constantine Hannaher
Assistant Examiner—Otilia Gabor
(74) Attorney, Agent, or Firm—Paul J. White

(57) ABSTRACT

A method for determining the mechanical properties of decayed wood that has been exposed to wood decay microorganisms, comprising:

a) illuminating a surface of decayed wood that has been exposed to wood decay microorganisms with wavelengths from visible and near infrared (VIS-NIR) spectra;

b) analyzing the surface of the decayed wood using a spectrometric method, the method generating a first spectral data of wavelengths in VIS-NIR spectra region; and c) using a multivariate analysis to predict mechanical properties of decayed wood by comparing the first spectral data with a calibration model, the calibration model comprising a second spectrometric method of spectral data of wavelengths in VIS-NIR spectra obtained from a reference decay wood, the second spectral data being correlated with a known mechanical property analytical result obtained from the reference decayed wood.

26 Claims, 3 Drawing Sheets

METHOD OF PREDICTING MECHANICAL PROPERTIES OF DECAYED WOOD

This invention is a continuation-in-part of U.S. Pat. application 09/740,293 filed Dec. 15, 2000.

CONTRACTUAL ORIGIN OF THE INVENTION

The United States Government has rights in this invention pursuant to Contract No. DE-AC36-99GO10337 between the United States Department of Energy and the Midwest Research Institute.

BACKGROUND OF THE INVENTION

1. Field of the Invention

The invention relates to the spectral analysis of wood, and in particular to a method of predicting mechanical properties of decayed wood that has been exposed to microorganisms by using light in a selected range of a visible and near infrared (VIS-NIR) spectrum.

2. Description of the Prior Art

A method for the nondestructive analysis of the quality of a tree, unlike conventional methods, which measure the volume and form of a tree, would provide important information to assist woodland owners in making their thinning decisions, and in the valuation of a stand of timber. The method would also be useful in the analysis of trees or sawn logs, in the woods, for the field sorting of logs to be used as poles, feedstocks in the manufacture of veneers, lumber or chips, or for measuring the strength of pole or wood used in utilities or structures.

Near infrared (NIR) spectroscopy, in combination with multivariate analysis (MVA) tools, is currently in use for the characterization of complex systems. These several statistical methods are also termed chemometric methods, forming the discipline of chemometrics, when applied generally to the field of chemistry, and in particular to the field of analytical chemistry. The technique of chemometrics is more fully explained in Brown, S. D., "Chemometrics", Anal. Chem. 62, 84R-101R (1990).

Also, near-infrared spectroscopy and chemometrics have been described for use in the non-destructive analysis of the chemical and physical properties of paper.

For example, U.S. Pat. No. 5,638,284 describes a method for the measurement of the wet strength of paper by analyzing the visible, near-infrared and/or infrared spectrum of the paper/pulp in the process line using a wavelength range within 400 nm to 4,000 nm, and applying a chemometric evaluation of the spectrum, to calculate the wet strength of the paper. Other examples include U.S. Pat. No. 5,680,321 (determining physical properties selected from dry tensile strength, hydrophobicity, debonding energy, bursting strength, wettability and printability in paper), and U.S. Pat. No. 5,680,320 (quantifying the amounts of reacted and/or retained chemical additives in paper by analysis of the visible, near-infrared and/or infrared spectrum of the paper/pulp in a process line).

While the foregoing art discloses the use of chemometric evaluation in the analysis of paper products, the entire NIR spectral range between 400 nm and 4,000 nm is used for the evaluation. Also, the mechanical properties of wet-solid-wood samples or wet or dry decayed wood are much more complex than those of paper due, in part, due to the presence of high concentrations of hemicellulose and lignin in wood relative to these components in paper. The structure and macromolecular morphology of the sample, such as roughness, color, and grain orientation also affect the spectral properties of solid wood. For a wet wood sample, the analysis of these properties is problematic because moisture in the samples, along with the high concentrations of lignin and hemicellulose tends to block or conceal the spectrometric derived information. Furthermore, many of these paper properties are a direct result of the presence of a small amount of an additive, or size or wet-strength resin, rather than a function of the inherent properties of paper fibers.

One example of the characterization of the NIR wood is described in U.S. Pat. No. 5,965,888, in which, NIR spectrometric data are obtained from dried wood chips. The method for the determination of parameters of wood panels comprises analyzing the raw wood chips/panels at a moisture content <10% by a spectrometric method to provide spectral data, and comparing the spectral data with reference spectral data from a reference chip/panel calibrated to known parameters of panels produced from the reference material, or of the reference panel by multivariate analysis. Again this method relies on the entire spectral range. This method is useful in predicting the quality of a dry wood panel based on an analysis of dried wood chips which are used as a feedstock in the manufacturing process.

NIR has also been used for determination of surface roughness and fiber angle of dry wood relative to the duration of the incident light, and for the evaluation of density and the strength of wood from a dry sample. See, e.g., Hoffmeyer, P., et al., Holz als Roh-und Werkstoff 53 (1995) 165–170.

In both U.S. Pat. No. 5,965,888 and Hoffmeyer, P., et al., Holz als Roh-und Werkstoff 53 (1995) 165–170, reference is explicitly made to the problems associated with measuring the NIR properties of wet wood, and seek to overcome them with use of a dry sample for analysis. All of these references use the full NIR spectral range, generally considered to be between 400 and 2,500 nm. Thus, they are using information from more than 2,000 individual wavelengths.

U.S. Pat. No. 5,945,676 disclose a method and apparatus for multi-spectral analysis in non-invasive NIR spectroscopy in which incident radiation containing a plurality of distinct, nonoverlapping spectral regions of wavelengths is used to irradiate the sample. Diffusively reflected radiation emerging from the sample is detected, and a value indicative of the concentration of the analyte is obtained, preferably using an application of chemometrics techniques.

A hand-held device for infrared reflectance measurements of samples to identify the sample material and comprising a self-contained portable unit built into a hand held housing is disclosed in U.S. Pat. No. 6,031,233. The housing includes a window and optics on a bench adjacent to the window, so that the optics are aligned with the sample when the device is placed directly against the sample. The optics include a broad-band IR light source shining onto an acousto-optic tunable filter (AOTF), which passes narrow-band IR light with a swept frequency; a lens focussing the radiation IR through the window onto the sample; and a reflectance detector aligned with the window of the housing to pick up reflected light. A computer, which may be mounted in the housing, compares the detected reflectance spectrum with stored sample data spectra, and identifies the material or the components of the material and their proportions.

However, none of the foregoing references are directed to measuring the mechanical properties of decayed wood that has been exposed to wood decay organisms, rather than changes in the chemical composition which are known to change as wood is decayed by microorganisms. And in many cases this decayed wood is also wet which further complicates the analysis.

A need therefore exists to measure the mechanical properties of decayed wood that has been exposed to microorganisms for predicting the serviceability and reliability of wood structures.

SUMMARY OF THE INVENTION

One object of the present invention is to provide a method for measuring the mechanical properties of decayed wood that has been exposed to microorganisms to enable predicting the serviceability and reliability of wood structures.

Another object of the present invention is to provide a method for measuring the mechanical properties of wood frames in houses and buildings, and wood poles used to support telephone, power lines, and marine structures that have been exposed to microorganisms that cause wood decay to enable predicting the serviceability and reliability of these wood frames and poles.

A further object of the present invention is to provide a practical device that can be used to collect and process VIS-NIR spectral data in a rapid and low cost method for measuring mechanical properties of decayed wood that has been exposed to microorganisms to enable predicting the serviceability and reliability of wood structures.

A still further object of present invention is to provide a process of utilizing VIS-NIR spectrum from about 400 to about 1,150 nm for measuring the strength of decayed wood that has been exposed to microorganisms that cause wood decay.

In general, the invention process is accomplished by gathering VIS-NIR spectra of wood that has been exposed to decayed organisms, and whose mechanical strength has been measured by some common analytical technique; using a first step where VIS-NIR spectra and mechanical strength values are used to construct a calibration model using multivariate statistical techniques; and using a second set of VIS-NIR spectra gathered from wood that has been exposed to decayed organisms, but whose strength is not known, and combining these spectra with the calibration model to predict the strength of the samples in the second set.

BRIEF DESCRIPTION OF THE DRAWINGS

The accompanying drawings, which are incorporated in and constitute a part of the specification, illustrate preferred embodiments of the invention and, together with the description establish the principles of the inventive concept.

DESCRIPTION OF THE PREFERRED EMBODIMENTS

Figure 1:
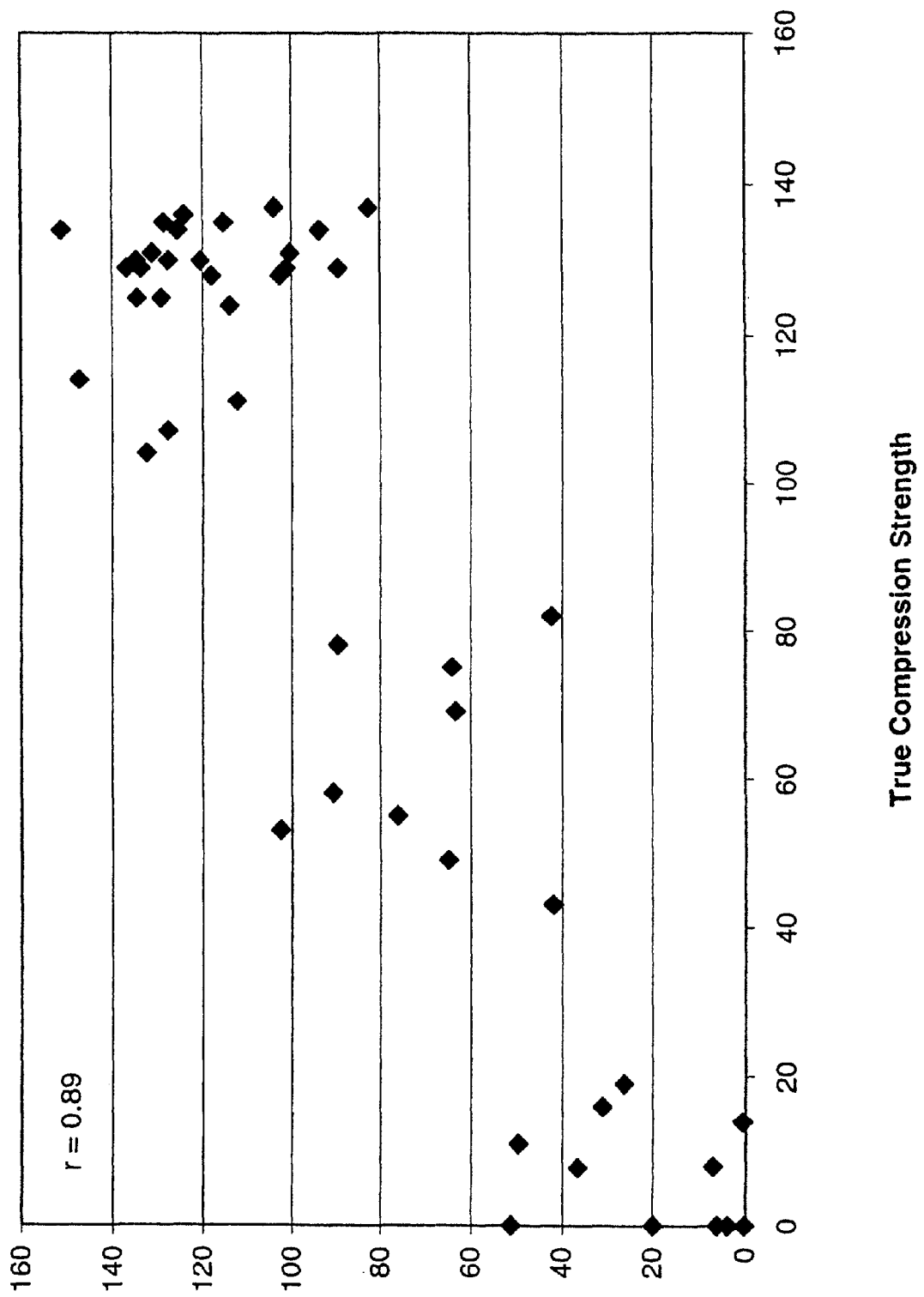
FIG. 1 is a plot of the true compression strength of southern pine samples exposed to wood decay organisms for varying lengths of time versus the strength predicted from the VIS-NIR spectra of the samples, wherein the prediction is based on the VIS-NIR spectral range of between 400 and 1,150 nm.

Unless specifically defined otherwise, all technical or scientific terms used herein have the same meaning as commonly understood by one of the ordinary skill in the art to which this invention pertains. Although any methods and materials similar or equivalent to those described herein can be used in the practice of the present invention, the preferred methods and materials are now described.

The invention utilizes a range of visible and near infrared (VIS-NIR) spectrum (400–1,150 nm) to measure the strength of wood that has been exposed to microorganisms that cause wood decay. Measuring the strength of wood that has been exposed to these microorganisms is useful for predicting the serviceability and reliability of wood structures. The structures include, but are not limited to, wood frames in houses and buildings, and wood poles used to support telephone, power lines and pilings for bridges and docks.

Further, in addition to the invention process of utilizing a range of the visible and near infrared spectrum for measuring the strength of wood that has been exposed to microorganisms that cause wood decay, the invention utilizes a practical device to collect and process VIS-NIR spectral data in a rapid and low cost method. The device relies on a reduced region of the VIS-NIR spectrum that can be easily accessed with low-cost, portable, hand-held VIS-NIR spectrometers.

Finally, the invention also describes the use of a reduced number of spectral points that can decrease the cost and size of a VIS-NIR spectrometer.

Significantly, the technology of the invention process constitutes a marked improvement over the current state-of-the-art which includes no monitoring of decay, the use of acoustical waves, or taking a core sample and culturing it for wood decay microorganisms. In fact, there is no monitoring of wood strength that has the obvious concern of giving the structural engineer no information until the wood piece has failed. In the case of wood structures, there is the possibility of injury to inhabitants, while in the case of utility poles, failure can lead to costly interruptions in electrical or telephone services.

Secondly, the VIS-NIR technology of the invention can be used to determine the strength of a wood piece in less than one minute in the field.

VIS-NIR in combination with MVA techniques, has been used to measure the chemical properties of mixtures. The VIS-NIR spectrum is generally considered to be between 400 and 2,500 nm; however, this invention only focuses on the use of a selected range of the VIS-NMR spectrum (400–1,150 nm).

Wavelengths between 400 and 1,1150 nm are the key aspect to this invention since there are commercially-available low-cost, lightweight spectrometers with very rapid acquisition times operating in this spectral range. While wavelengths between 400 and 1,150 nm contain overtones of many different carbon-hydrogen and hydroxyl vibrations, the exact assignment of specific chemical groups is not required for the effective use of this technology. The technology uses data processing algorithms such as projection of latent structures (PLS) modeling, orthogonal signal correction or wavelet transformation, to predict the mechanical properties of the wood and does not require precise assignment of the individual vibrations to specific chemical groups.

The second part of this invention process is the ability to use VIS-NIR to measure the strength of decayed wood using a fiber optic probe inserted into a piece of structural wood or pole tree. This is significant because it enables practical field sampling. A fiber optic probe inserted into the wood piece is coupled with a prism attached to the end of the probe that allows the spectra to be collected, preferentially from the radial face of the wood. This prism provides for illumination of the wood fibers and collects the reflectance spectrum from the wood.

The third part of the invention enables the use of fewer spectral data points. Over the VIS-NIR range of interest, the spectral data can be collected at 5 to 50 nm intervals without reducing the quality of the predictions. The spectral data can also be collected at 1 or 2 nm intervals and then averaged over 4 to 64 nm intervals without reducing the quality of the predictions.

EXAMPLE

The decayed wood samples were small blocks approximately 2 cm on a side in the radial and tangential directions and 0.5 cm thick in the longitudinal direction. The longitudinal face was placed on an agar plate that contained the wood decay fungi for 1 to 21 days. The weight loss and compression strength were measured on these samples. Compression strength was used because it is convenient to measure for these small samples, although other measures of strength and stiffness are expected to follow the same trends.

Control samples were prepared by placing end-matched blocks on agar plates that did not contain any decay fungi. The weight loss and crush strength of these samples were also measured. The percent strength loss was calculated by measuring the strength difference between the control and the end-matched decayed sample divided by the strength of the control times 100.

Reference is now made to FIG. 1, which is a plot of the true compression strength of decayed wood and the compression strength predicted with VIS-NIR at 400–1,150 nm. The plot of the true compression strength of southern pine samples exposed to wood decay organisms for varying lengths of time versus the strength is predicted from the VIS-NIR spectra of the samples. This figure clearly shows that compression strength of wood exposed to decay organisms varies widely, and that VIS-NIR can be used to detect these changes.

Figure 2:
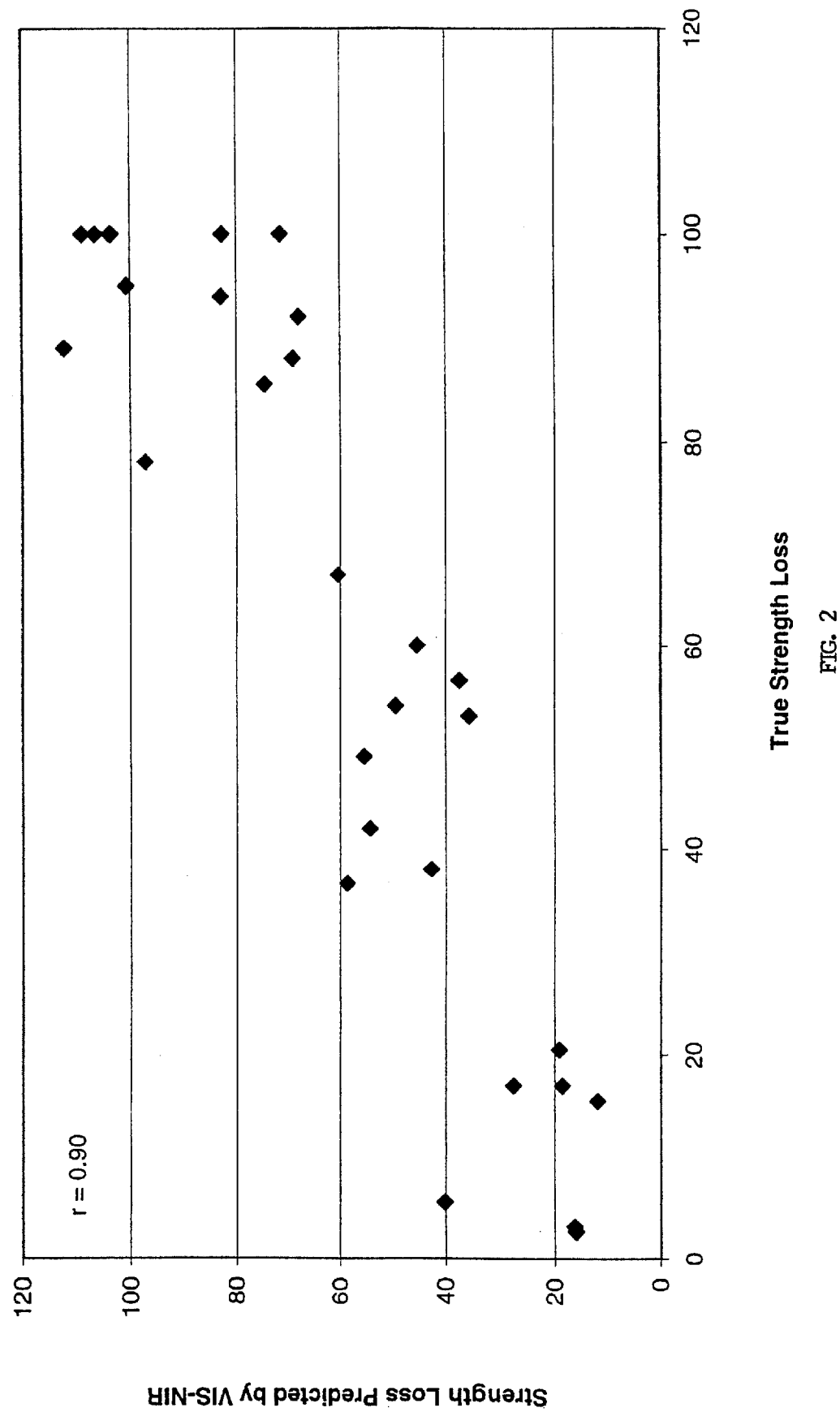
FIG. 2 is a plot of the strength loss of southern pine samples exposed to wood decay organisms for varying lengths of time versus the strength loss predicted from the VIS-NIR spectra of the samples, wherein the prediction is based on the VIS-NIR spectral range between 400 and 1,150 nm.

The graph of FIG. 2 shows the true strength loss of decayed wood and the strength loss predicted from the use of VIS-NIR at 400–1,150 nm. The plot of the strength loss of southern pine samples exposed to wood decay organisms for varying lengths of time versus the strength loss predicted from the VIS-NIR spectra of the samples is given. The strength loss measurement is the ratio of the compressive strength of a decayed sample to the compression strength of an "end-matched" piece of non-exposed southern pine whose compressive strength was already measured.

The quantitative examination of all the data was performed with projection to latent structures (PLS) modeling using the commercial computer software package THE UNSCRAMBLER sold by CAMO, Inc., although many similar products could also be used.

Figure 3:
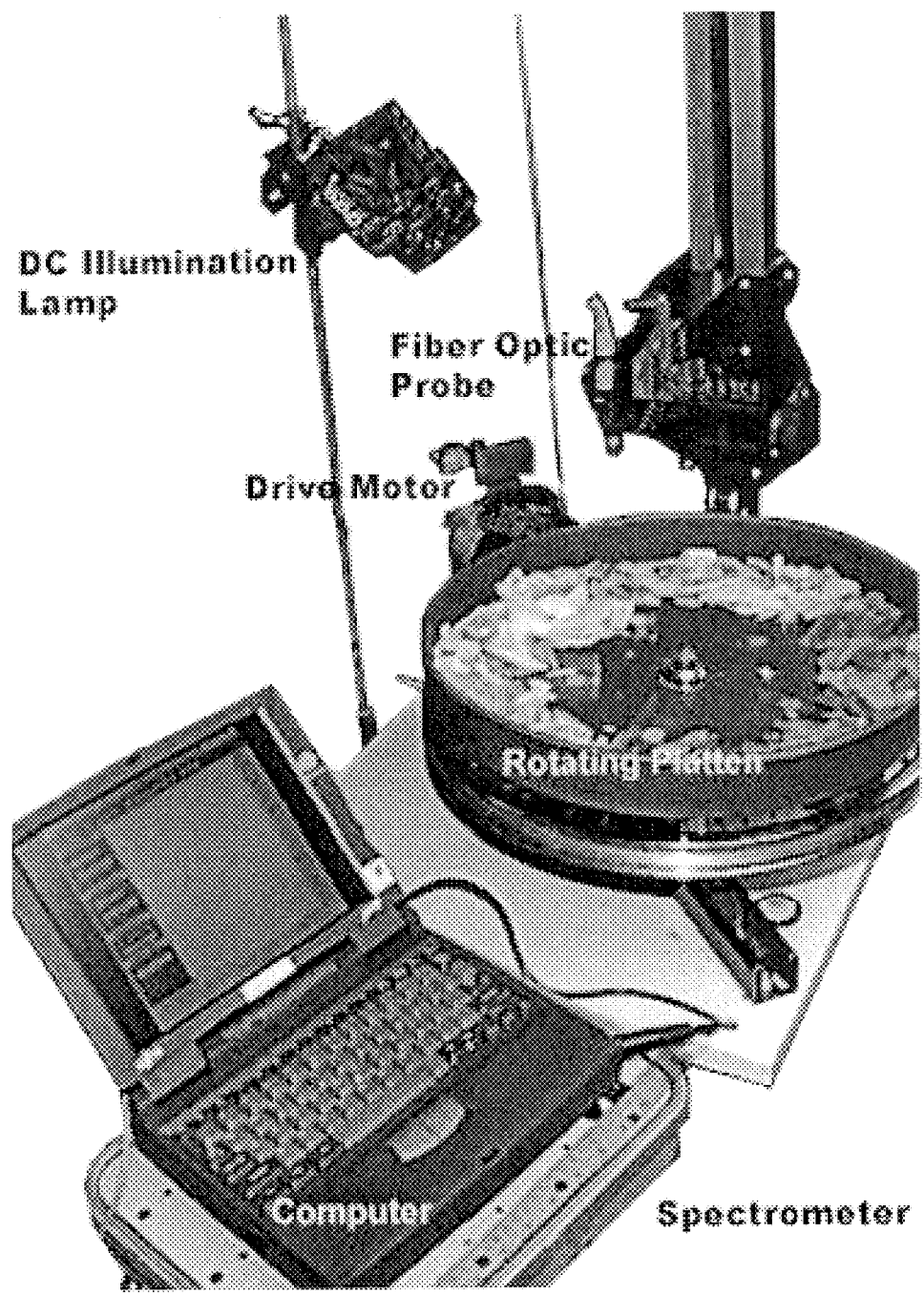
FIG. 3 is a photograph of an NIR spectrometer used to collect data on decayed wood.

The invention process also has the capability of using VIS-NIR to measure the strength of decayed wood using a fiberoptic probe, as may be seen from the photograph of FIG. 3, showing an NIR spectrometer that is used to collect data on decayed wood.

The fiberoptic probe is inserted into a piece of structural wood or pole tree. This is significant because it enables practical field sampling. The fiberoptic probe is inserted into the wood piece and is coupled with a prism attached to the end of the probe that allows the spectra to be collected preferentially from the radial face of the wood. This prism provides for illumination of the wood fibers and collects the reflectance spectrum from the wood.

The correlation coefficient (r) and root mean square error of prediction (RMESP) for the strength and strength loss percent of non-decayed and decayed wood predicted with NIR spectroscopy using different wavelength ranges are shown in Table I.

TABLE I

| Wavelengths (nm) | Strength | Strength Loss (%) |
|---|---|---|
| | Correlation Coefficients (r) | |
| 400–1150 | 0.89 | 0.90 |
| 400–700 | 0.87 | 0.87 |
| 500–800 | 0.86 | 0.88 |
| 600–900 | 0.84 | 0.87 |
| 700–1000 | 0.87 | 0.89 |
| 800–1100 | 0.88 | 0.91 |
| | Root Mean Square Error of Prediction (RMSEP) | |
| 400–1150 | 23.7 | 15.2 |
| 400–700 | 26.2 | 16.7 |
| 500–800 | 26.6 | 16.5 |
| 600–900 | 28.3 | 16.9 |
| 700–1000 | 26.3 | 15.9 |
| 800–1100 | 24.8 | 14.2 |

The r and RMESP for the strength and strength loss percent of non-decayed and decayed wood predicted with VIR-NIR spectroscopy using different wavelength ranges and averaged over different wavelength ranges is shown in Table II.

TABLE II

| Range of Wavelengths Averaged | Strength (400–1150 nm) | Strength Loss (%) (400–1150 nm) |
|---|---|---|
| | Correlation Coefficient | |
| 1 nm | 0.89 | 0.90 |
| 2 nm | 0.89 | 0.90 |
| 8 nm | 0.89 | 0.90 |
| 16 nm | 0.89 | 0.90 |
| 32 nm | 0.89 | 0.90 |
| 64 nm | 0.89 | 0.89 |
| 128 nm | 0.87 | 0.89 |
| | Root Mean Square Error of Prediction | |
| 1 nm | 23.7 | 15.2 |
| 2 nm | 23.7 | 15.2 |
| 8 nm | 23.7 | 15.2 |
| 16 nm | 23.6 | 15.2 |
| 32 nm | 23.6 | 15.2 |
| 64 nm | 23.9 | 15.5 |
| 128 nm | 25.7 | 15.4 |

The r and root mean square error of prediction RMESP for the strength and strength loss percentage of non-decayed and decayed wood predicted with VIS-NIR spectroscopy, using different wavelength ranges and averaged over different wavelength ranges is shown in Table III.

TABLE III

| Interval Measured | Strength (400–1150 nm) | Strength Loss (%) (400–1150 nm) |
|---|---|---|
| | Correlation Coefficient | |
| 1 nm | 0.89 | 0.90 |
| 20 nm | 0.89 | 0.89 |
| 50 nm | 0.90 | 0.90 |
| 100 nm | 0.89 | 0.89 |

TABLE III-continued

| Interval Measured | Strength (400–1150 nm) | Strength Loss (%) (400–1150 nm) |
|---|---|---|
| | Root Mean Square Error of Prediction | |
| 1 nm | 23.7 | 15.2 |
| 20 nm | 23.9 | 15.8 |
| 50 nm | 23.4 | 15.2 |
| 100 nm | 23.6 | 15.8 |

The experimental results in FIG. 1 shows the true compression strength and the compression strength predicted from the VIS-NIR spectra. The correlation coefficient for this prediction is 0.89. This plot highlights the value of the VIS-NIR technique for predicting the strength of decayed wood over a wide range of crush strength values.

The experimental results in FIG. 2 shows the true percent strength loss compared to the percent strength loss predicted from the VIS-NIR spectra. The correlation coefficient is 0.90. This plot highlights the value of VIS-NIR technique for predicting the strength loss of decayed wood over a wide range of strength values.

Tables I through III show the ability to use a reduced spectral range or fewer data points and still obtain high quality models of the strength of decayed wood. These results are significant as they highlight the capability of reducing the cost and weight of the VIS-NIR spectrometer, and also allow an increase in the sensitivity of the detectors.

More specifically, Table I shows the results of reducing the spectral range from the entire 400–1,150 nm interval to 300 nm intervals between 400–1,150 nm. This table shows that decreasing the spectral range to 300 nm intervals does not have a substantial negative impact on the quality of the PLS prediction for either strength or percent strength loss. The quality of the PLS predictions can be measured from both the r and the RMSEP of the PLS models. They are essentially unchanged when the spectral range is reduced from 400–1,150 nm to 300 nm intervals within this range.

The Table II shows the results of averaging the spectral data over different ranges. These averages were obtained by collecting data over the entire spectral range (400–1,150 nm) and then averaging the signal over different intervals. Reducing the number of spectral data points by averaging the signal does not reduce the quality of the PLS prediction, as measured by the r and the RMSEP of the PLS models.

Finally, the detailed specifics of Table III shows the results of reducing the number of spectral data points required for the models by taking a single spectral intensity at different intervals. Even with a very large sampling interval, e.g., 100 nm, the quality of the PLS prediction, as measured by the r and the RMSEP of the PLS models is not substantially decreased. This result is remarkable when one considers that a 100 nm sampling interval is only 8 spectral data points from the spectral range of 400–1,150 nm.

I claim:

1. A process for predicting mechanical properties of decayed wood exposed to wood decay microorganisms without monitoring the decay and without taking a core sample and culturing it for wood decay organisms, comprising:
   2) illuminating a surface of decayed wood exposed to wood decay microorganisms with wavelengths from visible and near infrared (VIS-NIR) spectra within the selected spectral range of about 400 to about 1,150 nm;
   2) analyzing the surface of said decayed wood using a spectrometric method, the method generating a first spectral data of wavelengths in VIS-NIR spectra region in said selected spectral range; and
   3) using a multivariate analysis to predict mechanical properties of decayed wood by comparing said first spectral data with a calibration model, said calibration model comprising a second spectrometric method of spectral data of wavelengths in VIS-NIR spectra said selected spectral range obtained from a reference decayed wood, the second spectral data being correlated with a known mechanical property analytical result obtained from said reference decayed wood.

2. The process of claim 1 wherein said multivariate analysis is selected from Projection to Latent Structures (PLS), Principal Component Analysis (PCA), Partial Least Squares Regression (PLSR), Principal Component Regression (PCR), Multilinear Regression Analysis (MLR) and Discriminant Analysis.

3. The process of claim 2 wherein a reduced spectral range from the entire 400–1,150 nm is employed in amounts of 300 nm intervals.

4. The process of claim 3 wherein said 300 nm interval is from 400 to 700 nm.

5. The process of claim 3 wherein said 300 nm interval is from 500 to 800 nm.

6. The process of claim 3 wherein said 300 nm interval is from 600 to 900 nm.

7. The process of claim 3 wherein said 300 nm interval is from 700 to 1,000 nm.

8. The process of claim 3 wherein said 300 nm interval is from 800 to 1,100 nm.

9. The process of claim 3 wherein said spectral data for data points are averaged over a range of wavelengths from 1 to 128 nm.

10. The process of claim 9 wherein the averaged wavelength is 1 nm.

11. The process of claim 9 wherein the averaged wavelength is 2 nm.

12. The process of claim 9 wherein the averaged wavelength is 8 nm.

13. The process of claim 9 wherein the averaged wavelength is 16 nm.

14. The process of claim 9 wherein the averaged wavelength is 32 nm.

15. The process of claim 9 wherein the averaged wavelength is 64 nm.

16. The process of claim 9 wherein the averaged wavelength is 128 nm.

17. The process of claim 9 wherein spectral data are obtained by taking a single spectral intensity at intervals measured from 1 to 100 nm.

18. The process of claim 17 wherein the interval measured is 1 nm.

19. The process of claim 17 wherein the interval measured is 20 nm.

20. The process of claim 17 wherein the interval measured is 50 nm.

21. The process of claim 17 wherein the interval measured is 100 nm.

22. The process of claim 1 wherein said mechanical property is strength.

23. The process of claim 22 wherein said strength is compression strength.

24. The process of claim 22 wherein said strength is bending strength.

25. The process of claim 22 wherein said strength is bending stiffness.

26. The process of claim 1 wherein said mechanical property is strength loss percent.

* * * * *